(12) United States Patent
Liu et al.

(10) Patent No.: US 10,119,932 B2
(45) Date of Patent: Nov. 6, 2018

(54) ELECTROCHEMICAL GAS SENSOR

(71) Applicant: Honeywell International Inc., Morristown, NJ (US)

(72) Inventors: Ling Liu, Shanghai (CN); Yan Zhang, Shanghai (CN); Qian Zheng, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 852 days.

(21) Appl. No.: 14/289,222

(22) Filed: May 28, 2014

(65) Prior Publication Data
US 2015/0346135 A1 Dec. 3, 2015

(51) Int. Cl.
| G01N 27/26 | (2006.01) |
| G01N 27/403 | (2006.01) |
| C23C 30/00 | (2006.01) |
| G01N 27/404 | (2006.01) |
| H01M 4/88 | (2006.01) |
| H01M 4/86 | (2006.01) |
| H01M 4/90 | (2006.01) |

(52) U.S. Cl.
CPC ........... *G01N 27/403* (2013.01); *C23C 30/00* (2013.01); *G01N 27/404* (2013.01); *G01N 27/4045* (2013.01); *H01M 4/8807* (2013.01); *H01M 4/8832* (2013.01); *H01M 4/8882* (2013.01); *H01M 4/8668* (2013.01); *H01M 4/8828* (2013.01); *H01M 4/90* (2013.01)

(58) Field of Classification Search
USPC ....................................................... 204/231
See application file for complete search history.

(56) References Cited

U.S. PATENT DOCUMENTS

| 5,716,437 A * | 2/1998 | Denton ...................... C25B 9/10 106/31.92 |
| 6,099,708 A * | 8/2000 | Mallory ............. G01N 27/4045 204/412 |
| 6,129,825 A * | 10/2000 | Mallory ............... G01N 33/004 204/415 |
| 7,022,213 B1 * | 4/2006 | Austen ................. G01N 27/404 200/264 |
| 2002/0105080 A1 * | 8/2002 | Speakman ................. B41J 2/01 257/749 |

(Continued)

FOREIGN PATENT DOCUMENTS

| CN | 103424456 A | 12/2013 |
| CN | 105277599 A | 1/2016 |

(Continued)

OTHER PUBLICATIONS

Lloyd, William J. et al, Ink Jet Printing, Output Hardcopy Devices, Boston, Academic Press, Jan. 1, 1987, pp. 311-370.

(Continued)

*Primary Examiner* — Jill A Warden
*Assistant Examiner* — Brittany I Fisher
(74) *Attorney, Agent, or Firm* — Wick Phillips Gould & Martin, LLP

(57) ABSTRACT

A gas detector includes an electrochemical gas sensor. The sensor includes a plurality of electrodes. At least one of the electrodes is formed of a catalyst/binder slurry which is halftone printed onto a substrate. The composite printed element and substrate are sintered to form the electrode.

5 Claims, 4 Drawing Sheets

(56) References Cited

U.S. PATENT DOCUMENTS

| | | | |
|---|---|---|---|
| 2002/0134501 A1* | 9/2002 | Fan | H01M 4/8807 156/308.2 |
| 2002/0197456 A1* | 12/2002 | Pope | G02F 1/133617 428/209 |
| 2004/0079637 A1* | 4/2004 | Maeno | G01N 27/403 204/431 |
| 2006/0102494 A1* | 5/2006 | Chueh | G01N 33/0037 205/785.5 |
| 2007/0045114 A1* | 3/2007 | Wang | C03C 8/14 204/431 |
| 2007/0102294 A1* | 5/2007 | Dorisio Deininger | G01N 27/4071 204/421 |
| 2007/0125664 A1* | 6/2007 | LaBarge | G01N 27/4071 205/780.5 |
| 2008/0209876 A1* | 9/2008 | Miller | G11C 13/0009 55/522 |
| 2008/0277290 A1* | 11/2008 | Jones | B01J 21/18 205/775 |
| 2009/0152113 A1 | 6/2009 | Chiu et al. | |
| 2009/0159445 A1* | 6/2009 | Krishna | G01N 27/4162 204/424 |
| 2009/0183999 A1* | 7/2009 | Ibarra | G01N 27/4071 205/775 |
| 2011/0262828 A1* | 10/2011 | Noda | H01M 4/8605 429/465 |
| 2012/0055789 A1* | 3/2012 | Swartz | G01N 27/403 204/415 |
| 2012/0125772 A1* | 5/2012 | Stetter | B32B 37/185 204/414 |
| 2012/0129077 A1* | 5/2012 | Hirakimoto | H01B 1/122 429/494 |
| 2012/0308907 A1* | 12/2012 | Peled | H01M 4/9083 429/417 |
| 2013/0175168 A1 | 7/2013 | Nemes | |
| 2013/0330590 A1* | 12/2013 | Toyoda | H01M 2/1653 429/142 |

FOREIGN PATENT DOCUMENTS

| | | |
|---|---|---|
| EP | 0902281 A2 | 3/1999 |
| EP | 0911632 A1 | 4/1999 |
| EP | 2950090 A1 | 12/2015 |
| WO | 9924826 A1 | 5/1999 |

OTHER PUBLICATIONS

EP15167776.2, Extended European Search Report, dated Sep. 29, 2015, 5 pages.

EP15167776.2, Communication pursuant to Rules 70(2) and 70a(2) EPC and reference to Rule 39(1) EPC dated Dec. 7, 2015, 2 pages.

China Patent Application No. 2015 1 0276809, First Office Action dated Jun. 29, 2018, 16 pages.

* cited by examiner

ELECTROCHEMICAL GAS SENSOR

FIELD

The application pertains to electrochemical gas sensors and gas detectors which incorporate such sensors. More particularly, the application pertains to such sensors which can be formed in part by printing.

BACKGROUND

Electrochemical gas sensors are well known for detecting and quantifying toxic gases such as carbon monoxide, oxygen and the like. Such sensors can be implemented using electrochemical cells. Such cells operate in an amperometric mode providing a current output which is related to the concentration of the particular analyte gas.

Such sensors usually include a sensing electrode. Known electrodes are made by a solution-based method.

In such solution-based methods, a catalyst is initially ultrasonically dispersed in an aqueous solution to form a suspension. Polytetrafluoroethylene (PTFE) is added to the suspension for form a flocculate mixture. The flocculate mixture is then transferred onto a substrate, which is sintered at an elevated temperature. The sintered mixture is then transferred onto a microporous PTFE membrane, then pressed. The ratio of PTFE in the electrode not only affects gas diffusion parameters in the sensor, it also supports the electrocatalyst and maximizes the interfaces between catalyst, gas and electrolyte at which the key electrochemical processes occur.

As is apparent, many steps are needed in this solution-based method to manufacture an electrode. The consequences include high manufacturing costs, material costs and labor costs.

DETAILED DESCRIPTION

Figure 1:
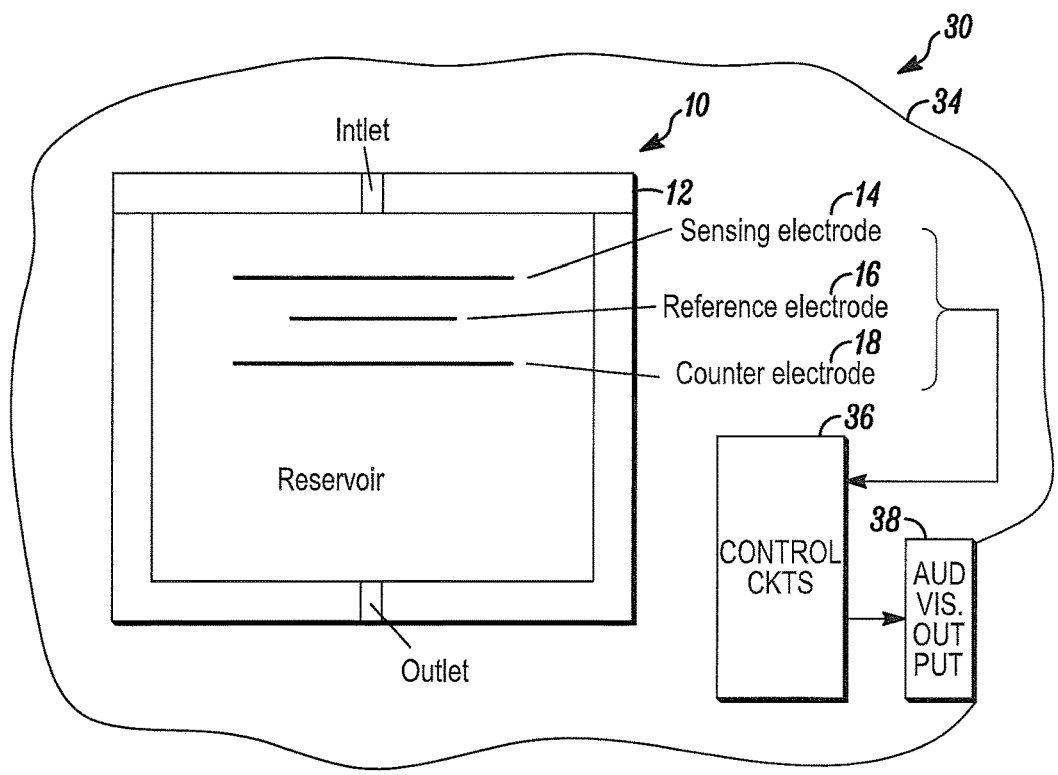
FIG. 1 illustrates a gas detector in accordance herewith.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

In one aspect, an electrochemical gas sensor having improved productivity can advantageously be implemented by using screen printing technology. A catalyst slurry, or recipe, can be screen printed or halftone printed on an electrode membrane by a printer, then sintered.

The printed element can then be used as an electrode of an electrochemical sensor. Exemplary types of sensors include $O_2$ sensors or CO sensors. In another aspect, alternative types of sensors in accordance herewith include, without limitation, oxygen pumps and toxic gas sensors.

The slurry can be made simply and quickly without any need for complicated equipment. The slurry can include a catalyst, binder, and diluents. Unlike known processes, the screen printing method, in accordance herewith, has fewer steps.

The catalyst can be platinum, platinum black, a mixture of graphite and platinum, a mixture of carbon and platinum black, a noble metal, mixtures thereof.

A solution of perfluorinated ion electrolyte solution (GEFC-IES the copolymer of perfluorosulfonic acid and PTFE) commercially available from Golden Energy Fuel Cell Co., Ltd. or Nafion® (copolymer of tetrafluoroethylene (Teflon®) and perfluoro-3,6-dioxa-4-methyl-7-octene-sulfonic acid) commercially available from Dupont™, can be used as a binder. Glycol or other similar chemicals can be used as a diluent to form a catalyst slurry, recipe or catalyst system, which can be printed on a PTFE membrane by a printer. The printed element is sintered at an elevated temperature to form an electrode which can be used in an electrochemical sensor such as $O_2$ sensor or CO sensor.

GEFC-IES's or Nafion®'s function is that of a binder. Its ratio in the electrode not only affects gas diffusion parameters in the sensor whilst supporting the electrocatalyst and maximizing the interfaces between catalyst, gas and electrolyte at which the key electrochemical processes occur. The slurry made from GEFC-IES or Nafion® is suitable for use in halftone screen printing.

As illustrated in FIG. 1, an exemplary oxygen sensor 10 can be carried in a housing 12 and include, a gas diffusion sensing or working electrode 14, a reference electrode 16 and a counter electrode 18. One or more of the electrodes can be formed by a printing process as described below in detail. The electrodes need not be identical.

As would be understood by those of skill in the art, electrodes formed by the present printing based process can be incorporated into gas detectors, such as detector 30. Detector 30 can include a housing 34 which carries the sensor 10, as well as electrodes 14-18 manufactured as described herein. Control circuits 36 can be coupled to the electrodes to make gas concentration determinations. An audio and/visual output device 38 can be provided to alert users to a current, sensed gas concentration.

Figure 2:
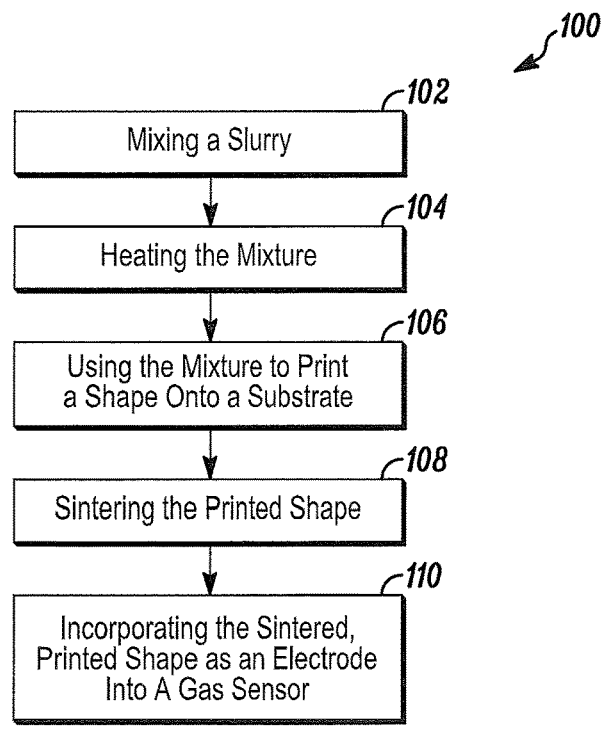
FIG. 2 is a flow chart illustrating aspects of a method in accordance herewith.

FIG. 2 illustrates aspects of a method 100 in accordance herewith. A slurry, including a platinum catalyst along with glycol and a solution of GEFC is mixed together to get a uniform mixture as at 102. The slurry is then heated, to a certain volume, as at 104.

The screen printable catalyst is then halftone printed on a PTFE sheet using a printer, as at 106. The printed element or shape is then sintered at a predetermined temperature, as at 108, to obtain an electrode which can be used as a sensing, reference, or counter electrode, as at 110.

In accordance herewith, the electrode catalysts can be made from 80% weight Platinum black and 20% weight of GEFC-IES binder. The binder in the slurry not only affects gas diffusion parameters in the sensor it also supports the platinum electrocatalyst and maximizes the interfaces between catalyst, gas and electrolyte at which the key electrochemical processes occur.

Relative to FIG. 1, sensor 10 can be implemented as a $O_2$ sensor or CO sensor using the electrode created by the above described process 100. Operationally, at the sensing electrode for an $O_2$ sensor the $O_2$ is reduced:

$$O_2 + 4H^+ + 4e^- \rightarrow 2H_2O \qquad (1)$$

At the counter electrode there is a counter balancing oxidation:

$$2H_2O \rightarrow 4H^+ + O_2 + 4e^- \qquad (2)$$

Figure 3:
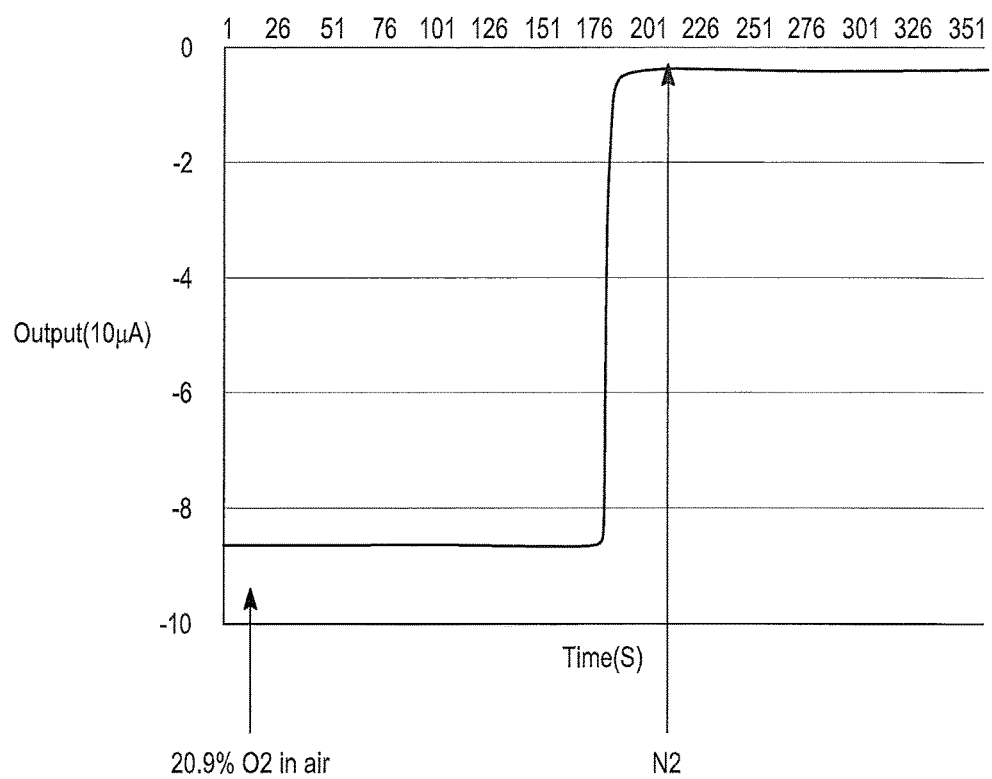
FIG. 3 is a graph illustrating response time to $O_2$ in air for an electrode including a mixture of GEFC-IES and platinum.

FIG. 3 illustrates a graph of the response of an $O_2$ sensor with time to 20.9% $O_2$ in air and $N_2$ with respect to the above described catalyst material. At a sensing electrode for a CO sensor the CO is oxidized:

$$CO + H_2O \rightarrow CO_2 2H^+ + 4e^- \qquad (3)$$

At the counter electrode there is a counter balancing reduction:

$$O_2 + 4H^+ + 4e^- \rightarrow 2H_2O \qquad (4)$$

Figure 4:
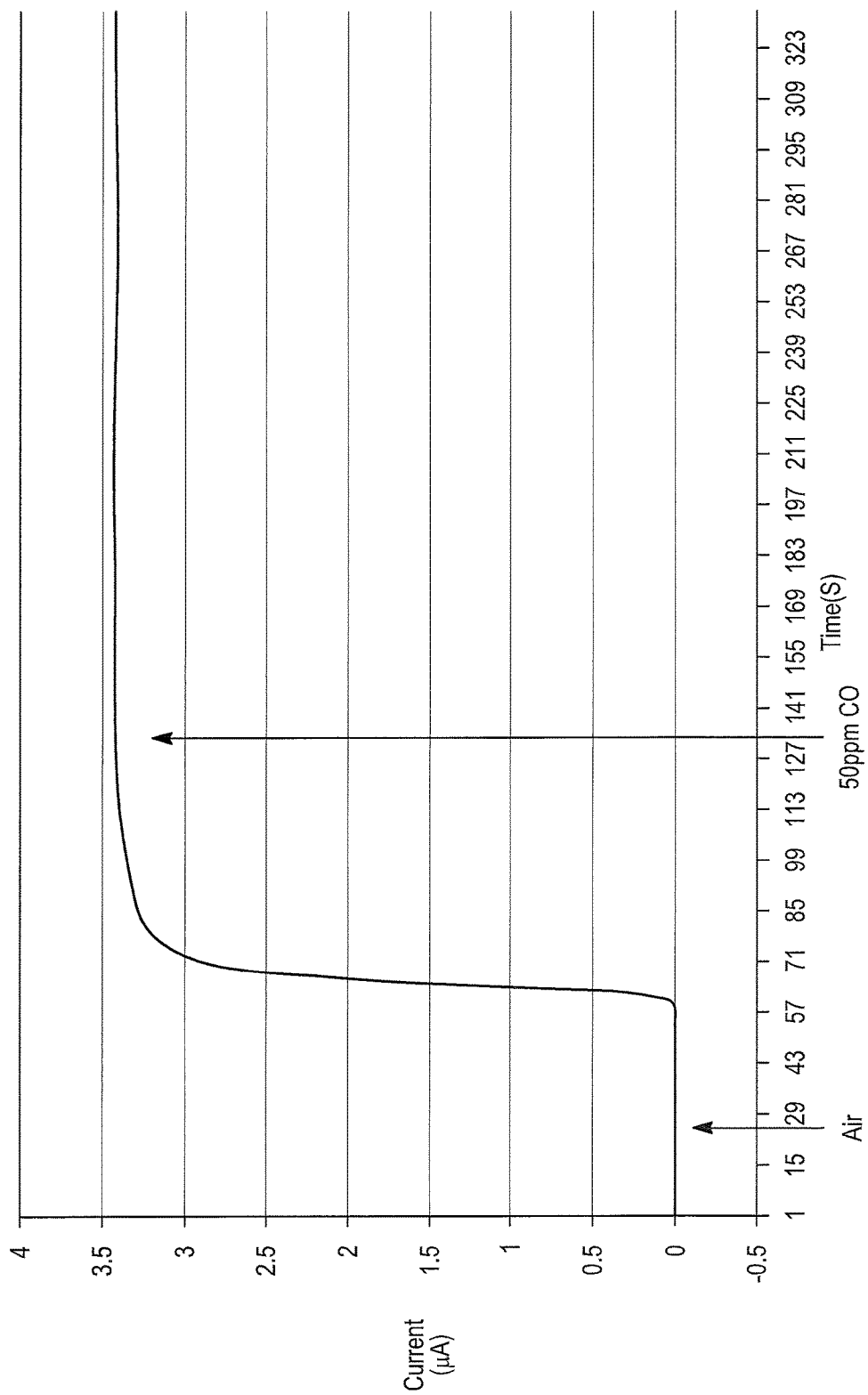
FIG. 4 is a graph illustrating response time to CO in air for an electrode including a mixture of GEFC-IES and platinum.

FIG. 4 illustrates a graph of the response with time to air and 50 ppm carbon monoxide using a mixture of GEFC-IES and Platinum as a sensing electrode formed by screen printing.

In another example a predetermined ratio of platinum and graphite is mixed together with glycol and a solution of GEFC-IES to get a uniform mixture. Then the slurry is heated to a predetermined volume. The catalyst is then halftone printed on a PTFE sheet using a printer. After printing, the printed element is then sintered at a predetermined temperature to obtain the electrode which can be used as a sensing, reference, or counter electrode for an $O_2$ sensor.

Figure 5:
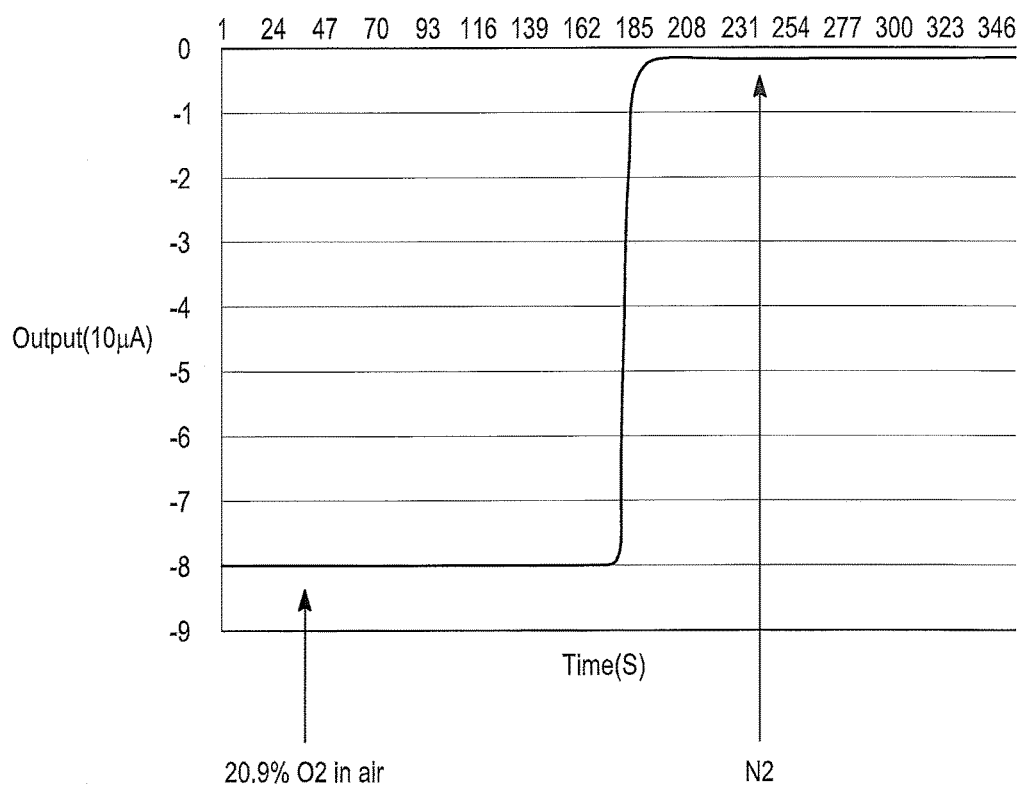
FIG. 5 is a graph illustrating response time to $O_2$ in air for an electrode including a mixture of GEFC-IES, platinum and graphite.

The electrode catalyst in this second example is made from 75% weight Platinum black, 10% weight graphite and 15% weight GEFC-IES binder. FIG. 5 illustrates a graph of the response to $O_2$ sensor with time in air and $N_2$ with respect to the second catalyst material.

In summary, the above disclosed electrode manufacturing process using screen printing method has fewer steps than known processes. First, a catalyst (e.g. Platinum Black or mixture of Carbon and Platinum Black or other noble metal catalyst) is mixed with GEFC-IES or Nafion® or a mixture of GEFC-IES and Nafion®. Glycol is then added to form a slurry by stirring.

An electrode form can then be screen printed on a PTFE membrane and sintered at an elevated temperature. Platinum electrodes usable in both sensors and CO sensors can be formed using this screen printing process.

Those of skill will also understand that the graphs of FIG. 3-5 are illustrative only and not limitations hereof. Variations in electrode structures may lead to differing response times without departing from the spirit and scope hereof.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A method comprising:
heating a slurry prior to halftone printing the slurry;
providing the slurry comprising at least a catalyst and a binder;
halftone printing the slurry in a selected shape onto a porous substrate;
sintering the printed shape and associated substrate; and
incorporating the sintered shape and the associated substrate as an electrode into an electrochemical sensor;
wherein a composition of the slurry comprises 75% weight Platinum black, 10% weight graphite and 15% weight perfluorinated ion electrolyte solution;
wherein a response time for the electrochemical sensor comprising the composition is between 24 and 47 seconds for 20.9% oxygen in air.

2. A method comprising:
heating a slurry prior to halftone printing the slurry;
providing the slurry comprising at least a catalyst and a binder;
halftone printing the slurry in a selected shape onto a porous substrate;
sintering the printed shape and associated substrate; and
incorporating the sintered shape and the associated substrate as an electrode into an electrochemical sensor;
wherein the slurry further comprises a diluent comprising glycol;
wherein a response time for the electrochemical sensor is between 231 and 254 seconds for nitrogen.

3. A method as in claim 2, wherein the binder comprises a perfluorinated ion electrolyte solution.

4. A method as in claim 2, wherein the catalyst comprises at least one of: platinum, platinum black, a mixture of graphite and platinum, a mixture of carbon and platinum black, a noble metal, or mixtures thereof.

5. A method as in claim 4, wherein the binder comprises at least one of a perfluorinated ion electrolyte solution or a copolymer of tetrafluoroethylene and a sulfonic acid.

* * * * *